United States Patent
van Kampen et al.

(10) Patent No.: US 12,329,555 B2
(45) Date of Patent: Jun. 17, 2025

(54) COMPACT IMAGING DEVICE AND SYSTEM

(71) Applicant: Xoran Technologies, Inc., Ann Arbor, MI (US)

(72) Inventors: William van Kampen, Saline, MI (US); Miodrag Rakic, Saline, MI (US); Francisco Gomez Ruiz, Novi, MI (US); Andrew Custer, Saline, MI (US); Dejan Teofilovic, Ann Arbor, MI (US); Lauren Long, Ann Arbor, MI (US); David Sarment, Saline, MI (US)

(73) Assignee: Xoran Technologies LLC, Ann Arbor, MI (US)

(*) Notice: Subject to any disclaimer, the term of this patent is extended or adjusted under 35 U.S.C. 154(b) by 191 days.

(21) Appl. No.: 18/112,334

(22) Filed: Feb. 21, 2023

(65) Prior Publication Data

US 2023/0263488 A1 Aug. 24, 2023

Related U.S. Application Data

(60) Provisional application No. 63/311,758, filed on Feb. 18, 2022.

(51) Int. Cl.
*A61B 6/00* (2006.01)
*A61B 6/03* (2006.01)

(52) U.S. Cl.
CPC ............ *A61B 6/4405* (2013.01); *A61B 6/035* (2013.01); *A61B 6/4441* (2013.01); *A61B 6/56* (2013.01)

(58) Field of Classification Search
CPC ..... A61B 6/4405; A61B 6/035; A61B 6/4441; A61B 6/56
See application file for complete search history.

(56) References Cited

U.S. PATENT DOCUMENTS

| | | | |
|---|---|---|---|
| 6,466,641 B1 | 10/2002 | Virta et al. | |
| 7,379,524 B2 | 5/2008 | Bair | |
| 9,414,791 B2 | 8/2016 | Jun | |
| 9,662,086 B2 | 5/2017 | Ohta et al. | |
| 10,952,688 B2 | 3/2021 | Rakic et al. | |
| 2005/0135560 A1* | 6/2005 | Dafni | A61B 6/56 378/101 |
| 2015/0342543 A1* | 12/2015 | Khen | G06T 11/005 250/362 |

FOREIGN PATENT DOCUMENTS

| | | | |
|---|---|---|---|
| CN | 106926266 A | 7/2017 | |
| EP | 2676627 A2 * | 12/2013 | ............ A61B 34/20 |
| KR | 20170128589 A * | 11/2017 | ........... A61B 6/4482 |

OTHER PUBLICATIONS

International Search Report of corresponding PCT application PCT/US2023/062942, dated Jul. 19, 2023.

* cited by examiner

*Primary Examiner* — Dani Fox
*Assistant Examiner* — Fani Polyzos Boosalis
(74) *Attorney, Agent, or Firm* — K&L Gates LLP

(57) ABSTRACT

An imaging system includes components to allow the system to be compact, highly transportable, and capture images in non-conventional settings. An imaging device includes an exoskeleton configured to house and provide structural support for an x-ray source and a detector and a spindle structure protruding from an outer surface of the exoskeleton. The imaging device also includes an x-ray source and a detector affixed to an internal surface of the exoskeleton and a rotation motor configured to rotate the exoskeleton about the spindle structure.

16 Claims, 11 Drawing Sheets

COMPACT IMAGING DEVICE AND SYSTEM

CROSS REFERENCE TO RELATED APPLICATIONS

This application claims the benefit of priority to U.S. Provisional Application No. 63/311,758 filed Feb. 18, 2022, which is hereby incorporated by reference.

BACKGROUND OF THE INVENTION

The present subject matter relates generally to a point of care imaging device. More specifically, the present invention relates to a compact, lightweight, and optionally foldable imaging device, such as an x-ray, fluoroscopy, or computed tomography (CT) scanner, that can allow imaging capabilities in otherwise non-addressable environments, such as on an aircraft, in an ambulance, on a ship, or on a space station. The device may be used for either medical or non-medical imaging applications.

Traditional CT scanners typically weigh around 1,000 pounds. The weight of the scanner is in part attributed to the construction of conventional medical imaging devices. The electrical components are typically mounted on an internal structure, such as a metal plate or frame, while a protective covering surrounds the system to protect the components and provide a nice appearance. Large slip rings are used to conduct power and signals into the imaging components on the rotating internal imaging gantry. These components each add significant weight and cost to the system. Additionally, the x-ray emitter and the detector usually have a fixed rigid relationship with respect to each other, which allows for repeatability in image capturing, but can make the device very large and unwieldy.

The size and weight of conventional scanners typically require a dedicated room for operation since the scanner is not easily transported. This requires imaging to be done in designated medical imaging rooms, which is not convenient in emergency or remote situations and does not provide for immediate care, especially in situations where timing is critical.

To remedy this issue, point of care CT scanners have been developed, however, these scanners still typically weigh approximately 500 pounds or more and are usually at least 3×3×5 feet in volume. For example, U.S. Pat. No. 7,379,524, the entirety of which is incorporated herein by reference, discloses a compact CT scanner that contains all the essential elements needed for imaging, such as the computer for acquiring images, and the rotation motor, in addition to the x-ray source and detector. U.S. Pat. No. 10,952,688 B2, the entirety of which is incorporated herein by reference, discloses a modular imaging arm with a central spindle and safety locking mechanism, among other attributes, and various deployment scenarios. These "state-of-the-art" imaging devices still do not provide an on the site, transportable imaging device for point of care medical imaging.

Accordingly, there is a need for a point of care imaging device that is compact, lightweight, highly transportable, and could be used to capture images in non-conventional settings beyond a dedicated room in a medical facility.

BRIEF SUMMARY OF THE INVENTION

To meet the needs described above and others, the present disclosure provides an imaging system that is compact, lightweight, highly transportable, and could be used to take images in non-conventional settings beyond a dedicated room in a medical facility. The disclosed imaging devices and systems have non-medical applications as well, such as scanning packages, baggage, or other objects of interest in unconventional settings where larger systems are impractical to deploy, such as in a sports stadium or on a battlefield.

For some medical emergencies, timing is critical. For example, in patients undergoing a stroke, the term 'golden hour' is used by medical professionals to describe the first hour after a patient experiences a stroke. During this first hour, patients have a much greater chance of surviving and avoiding long-term brain damage if they arrive at the hospital and receive treatment with a clot-busting drug called TPA within that time frame.

However, particularly in remote locations, it is not always possible to transport a patient from the site of the stroke to a hospital in this window. Therefore, the imaging device of the present invention provides an alternative to the conventional approach and can allow a medical professional to take point-of-care image right on the site, enabling interventions which could greatly affect the outcome for the stroke patient.

The present disclosure also provides systems, devices, and methods for obtaining a brain CT with injected contrast material looking for Large Vessel Occlusion (LVO) or for obtaining a multi-orbit Head CT Perfusion (CTP) imaging to assess recoverable penumbra and determine patient routing to most appropriate treatment facility. These are just a few examples of how the present disclosure can provide life-saving solutions on the site in limited time.

In one embodiment, the imaging device of the present application includes an exoskeleton, an x-ray source, a detector, and a rotation motor. The exoskeleton can replace the need for an inner frame structure, thus saving system weight and can be a hollow structure. In one embodiment, the exoskeleton includes a base portion, a first side portion, and a second side portion. The side portions may connect to the base portion through hinging mechanisms that allow the side portions to fold into the base portion to provide a compact configuration for easier transport. The base portion may include a spindle structure which is generally aligned with the axis of gantry rotation attached to the outer surface of the base portion. A small slip ring positioned about a spindle may be employed to conduct power and electronic signals between the non-rotation connection point and the internal rotating components and allow freedom from cables which become twisted and worn as well as allow continuous rotation for multi-orbit scanning protocols without the needs for rotating the opposite direction to unwind.

When in use, the imaging device may include locking mechanisms on the exterior of the exoskeleton that are used to lock the first side portion and second side portion to the base portion in a gantry assembly and prevent movement of the side portions about the hinges. Each locking mechanism may be a toggle latch or any other suitable locking mechanism.

The imaging elements may be affixed to the interior hollow compartment of the exoskeleton. This "exoskeleton" design approach combines the functionality of the metal inner frame traditionally used for mounting electrical components and the external cover of conventional imaging systems. The combination provides a lighter weight device. The exoskeleton may be constructed of a material such as carbon fiber, which is strong and light and also sufficiently radiolucent that it allows the x-rays to pass through, enabling a seamless closed design on both x-ray source and detector sides of the system.

The present disclosure also provides an imaging system including the imaging device described herein and a support frame that holds the imaging device in position for use on a patient. For example, the support frame may position the imaging device in a vertical orientation, where the spindle structure extends vertically, or in a horizontal position, where the spindle structure extends horizontally. The support frame may include a bore configured to engage with the spindle structure of the imaging device. The support frame is configured to rest on a support surface and provides support and stability to the imaging device while the imaging device is free standing.

In some embodiments, the support frame includes a plurality of legs extending from a bracket. A bushing may be attached to the bracket and the bore may extend through the bracket and the bushing. In this configuration, the central axis of the bore extends perpendicular to the support surface on which the support frame rests. The plurality of legs may rotate about the bracket from an operable position to a stored position.

In some embodiments, the support frame includes a cart-like structure with a base portion and a side portion. The bore can be affixed to the side portion and the central axis of the bore may extend parallel to the support surface on which it rests. The side portion may also fold into the base portion for storage and transportation. This cart may or may not be on wheels.

The imaging system may additionally include a robot, such as a wheeled or stationary robot. The robot may include an arm configured to hold the imaging device. The robot may function similar to the other support structures by providing stability in a free standing configuration while capturing images or the robot may be used for transportation of the imaging device and/or the support structure.

Another aspect of the present disclosure provides a method for acquiring an image using the imaging device disclosed herein, the method including the steps of configuring and positioning the imaging device, specifically around the object being captured, and capturing an image. Different types of images can be captured from the imaging device including x-ray, fluoroscopy, and computed tomography (CT).

In light of the disclosure set forth herein, and without limiting the disclosure in any way, in a first aspect, which may be combined with any other aspect or portion thereof described herein, an imaging device includes an exoskeleton comprising a base portion, a first side portion, and a second side portion. In some embodiments, a first inner end of the first side portion connects to the base portion through a first hinge mechanism, and a second inner end of the second side portion connects to the base portion through a second hinge mechanism. In other embodiments, the base portion, the first side portion, and the second side portion are integrally formed. The imaging system also includes a spindle structure protruding from an outer surface of the base portion, an x-ray source mounted within the first side portion, a detector mounted within the second side portion, and a rotation motor configured to rotate the exoskeleton about the spindle structure. In some embodiments, the rotation motor is affixed to the exoskeleton within the base portion.

In a second aspect, which may be combined with any other aspect or portion thereof described herein unless otherwise specified, the imaging device includes one or more locking mechanisms configured to prevent the first side portion and the second side portion, respectively, from moving about the first hinge mechanism and the second hinge mechanism, respectively.

In a third aspect, which may be combined with any other aspect or portion thereof described herein unless otherwise specified, the locking mechanism comprises a toggle latch.

In a fourth aspect, which may be combined with any other aspect or portion thereof described herein unless otherwise specified, the spindle structure extends through the outer surface of the base portion.

In a fifth aspect, which may be combined with any other aspect or portion thereof described herein unless otherwise specified, the imaging device further comprises a support frame including a bracket and a plurality of legs, each leg rotatably connected to the bracket, wherein the support frame is configured to move between an operable position and a stored position.

In a sixth aspect, which may be combined with any other aspect or portion thereof described herein unless otherwise specified, each leg includes multiple segments connected by hinges.

In a seventh aspect, which may be combined with any other aspect or portion thereof described herein unless otherwise specified, the spindle structure comprises a cylindrical member.

In an eighth aspect, which may be combined with any other aspect or portion thereof described herein unless otherwise specified, the first side portion and the second side portion are configured to fold toward the base portion.

In a ninth aspect, which may be combined with any other aspect or portion thereof described herein unless otherwise specified, the imaging device comprises a circuit board, a control PC, and an optional Wi-Fi communication module, wherein the circuit board, the control PC, and the Wi-Fi communication module are mounted to an interior compartment of the exoskeleton. In some embodiments, an antenna is provided external to the exoskeleton for wireless communication with external devices.

In a tenth aspect, which may be combined with any other aspect or portion thereof described herein unless otherwise specified, an imaging system is provided. The imaging system includes an imaging device including an exoskeleton comprising a base portion, a first side portion, and a second side portion; a spindle structure protruding from an outer surface of the base portion; an x-ray source mounted within a first outer end of the first side portion; a detector mounted within a second outer end of the second side portion; and a rotation motor configured to rotate the exoskeleton about the spindle structure; a support frame that includes a bore, wherein the spindle structure of the exoskeleton is positioned within the bore during use.

In an eleventh aspect, which may be combined with any other aspect or portion thereof described herein unless otherwise specified, the support frame is positioned on a support surface, and wherein the bore of the support frame has a central axis that extends parallel to the support surface.

In a twelfth aspect, which may be combined with any other aspect or portion thereof described herein unless otherwise specified, the support frame comprises a base portion and a side portion, wherein the side portion extends from the base portion.

In a thirteenth aspect, which may be combined with any other aspect or portion thereof described herein unless otherwise specified, the support frame is positioned on a support surface, and wherein the bore of the support frame has a central axis that extends perpendicular to the support surface.

In a fourteenth aspect, which may be combined with any other aspect or portion thereof described herein unless otherwise specified, the support frame includes a plurality of legs extending from a bracket, wherein the plurality of legs move between an operable position and a stored position.

In a fifteenth aspect, which may be combined with any other aspect or portion thereof described herein unless otherwise specified, the bracket includes a bushing attached to a base, and wherein the bore extends through the base and the bushing, wherein each leg includes an inner end and an outer end, and wherein the inner ends of the plurality of legs are secured in the base and circumscribe the bushing when the plurality of legs is in the operable position.

In a sixteenth aspect, which may be combined with any other aspect or portion thereof described herein unless otherwise specified, the imaging system further comprises a robot comprising an arm configured to hold the imaging device.

In a seventeenth aspect, which may be combined with any other aspect or portion thereof described herein unless otherwise specified, a method of acquiring a scan of a patient is provided. The method includes the steps of providing an imaging system comprising an imaging device comprising an exoskeleton comprising a base portion, a first side portion, and a second side portion, wherein a first inner end of the first side portion connects to the base portion through a first hinge mechanism, and wherein a second inner end of the second side portion connects to the base portion through a second hinge mechanism, wherein the exoskeleton includes a spindle structure on an outer surface of the base portion that provides access to an interior of the exoskeleton; an x-ray source mounted within a first outer end of the first side portion; a detector mounted within a second outer end of the second side portion; and a rotation motor configured to rotate the exoskeleton about the spindle structure; and a support frame that includes a bore, wherein the spindle structure of the exoskeleton is positioned within the bore during use; securing the imaging device within the support frame; positioning the patient between the first and second side portions of the imaging device; and capturing an image using the x-ray source and the detector of the imaging device.

In an eighteenth aspect, which may be combined with any other aspect or portion thereof described herein unless otherwise specified, capturing an image comprises capturing one or more x-ray projection images.

In a nineteenth aspect, which may be combined with any other aspect or portion thereof described herein unless otherwise specified, capturing an image comprises capturing one or more x-ray projection images, adjusting the positioning of the imaging device, and capturing additional x-ray projection images. For example, the method may include rotating the exoskeleton about the axis of rotation, and the step of capturing an image comprises capturing a plurality of x-ray projection images as the exoskeleton rotates about the axis of rotation. The method may then further include tomographically reconstructing the plurality of x-ray projection images into a CT image volume.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
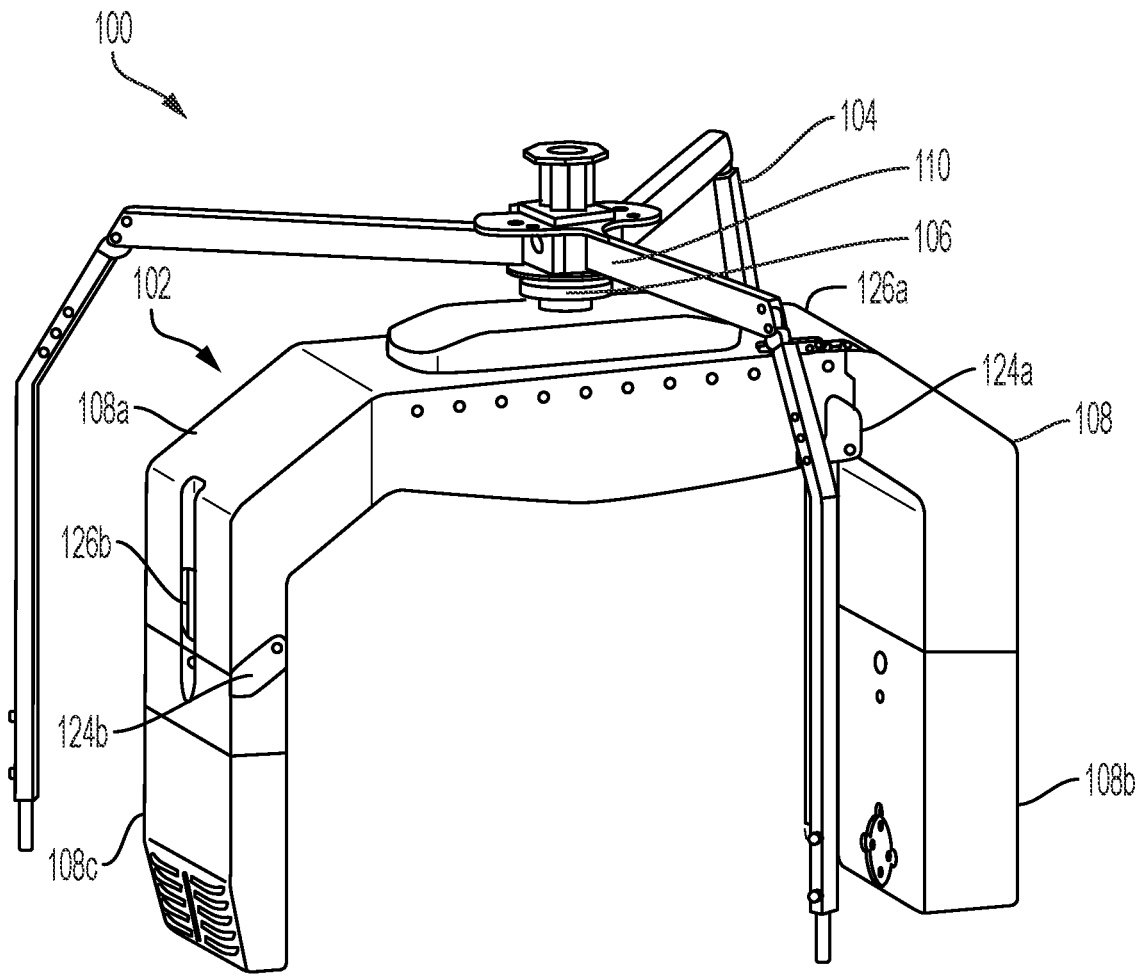
FIG. 1 is a perspective view of an embodiment of an imaging device of the present application mounted on a support frame with a vertical axis of rotation.

FIGS. 1-15 illustrate example embodiments of compact, lightweight, highly transportable imaging systems 100, 200, 300 of the present application. The portable imaging systems 100, 200, 300 enable a physician or operator to take images of a target object in unconventional settings beyond a dedicated room in a medical facility or an x-ray baggage screening system at an airport. The target object may be a patient or an object, such as baggage, a package, or other container.

In the embodiment illustrated in FIGS. 1-7, the imaging system 100 includes an imaging device 102 that moves between a compact, folded position and a locked, operable position, while the imaging system 200, 300 of FIGS. 11-14 includes an imaging device 202 that is non-foldable. During use, the imaging device 102, 202 is mounted within a support frame 104, 204 such that the device is freestanding and able to rotate about a patient as needed.

Figure 11:
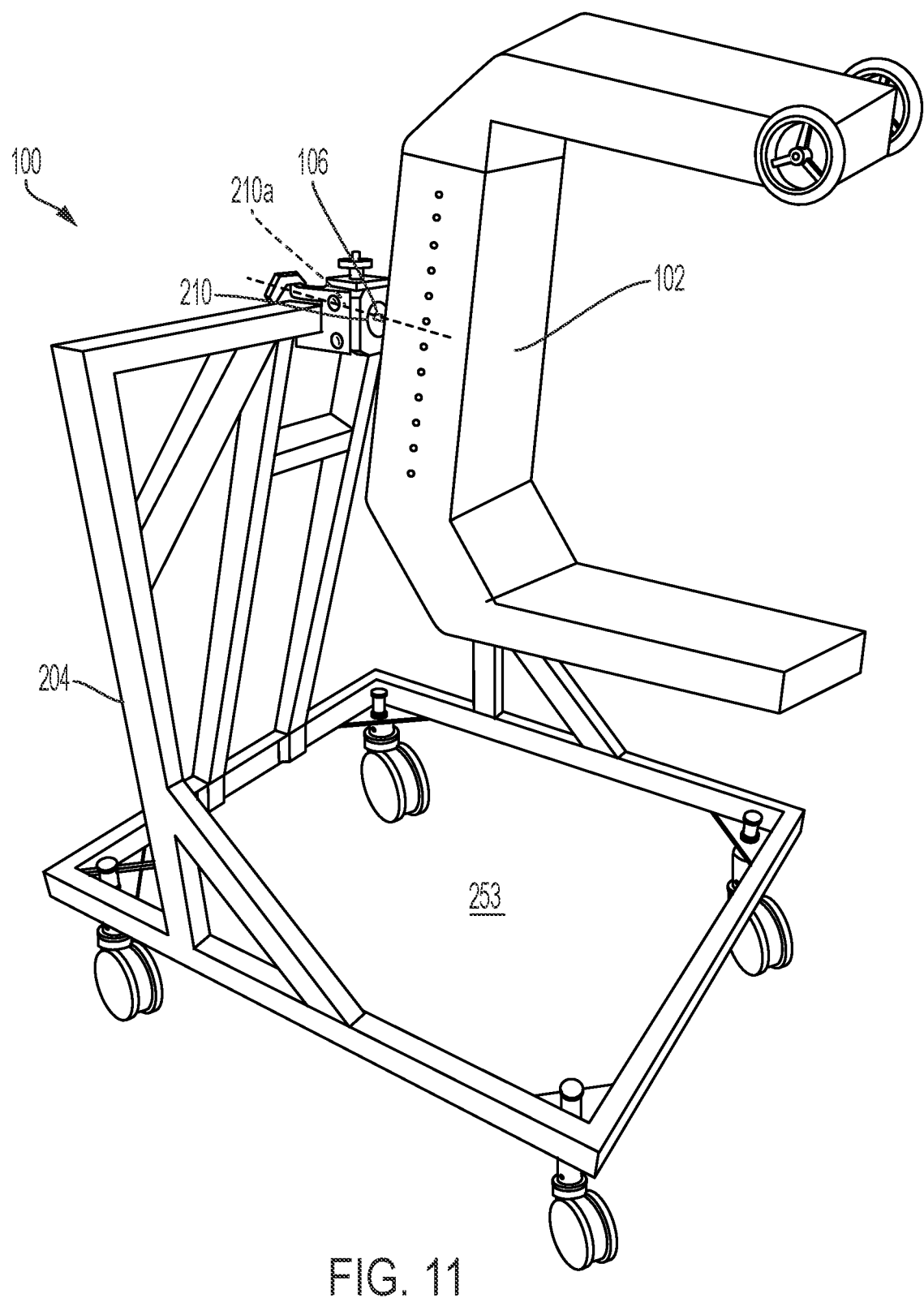
FIG. 11 is a perspective view of another embodiment of an imaging device of FIG. 1 mounted on a further embodiment of the support frame with a horizontal axis of rotation.
Figure 12:
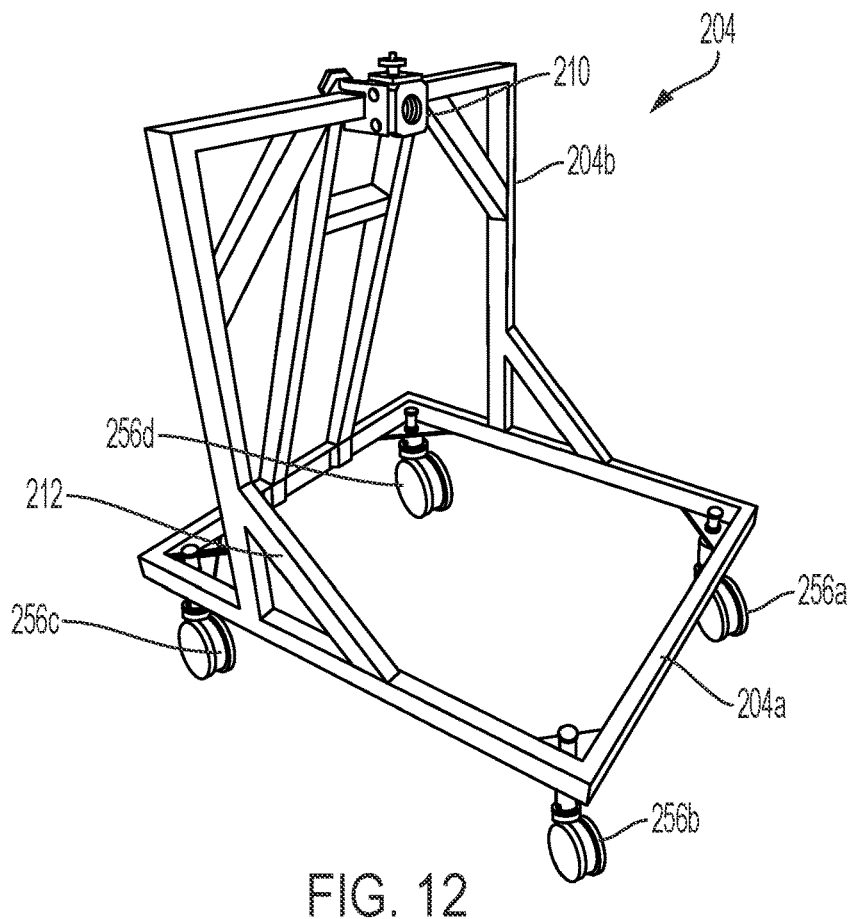
FIG. 12 shows a perspective view of the support frame of FIG. 11.
Figure 13:
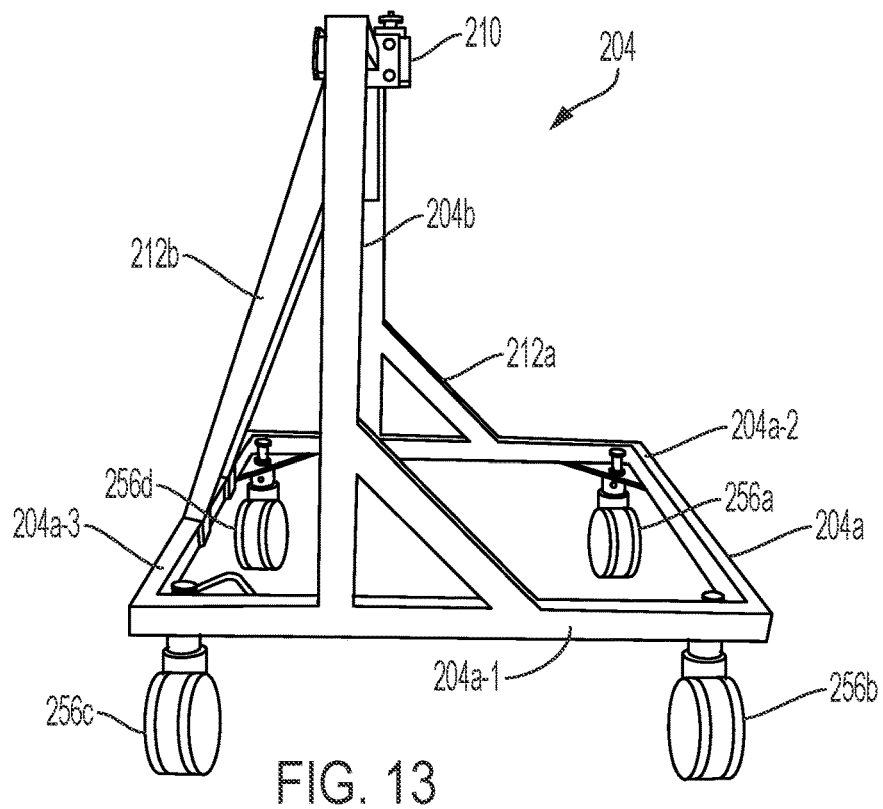
FIG. 13 shows a side elevational view of the support frame of FIG. 11.

FIGS. 1-7 illustrate a first embodiment of a support frame 104 that allows the imaging device 102 to maintain a vertically-oriented position, while FIGS. 11-13 illustrate a second embodiment of the support frame 204 that maintains the imaging device 202 in a horizontally-oriented position. In both embodiments, the imaging device 102, 202 is mounted to the support frame 104, 204 so that it rotates freely about an axis of rotation 106a, 206a defined by the spindle structure 106, 206 held within the support frame 104, 204. While the foldable imaging device 102 is shown with the vertical-orientation support frame 104 and the non-foldable imaging device 202 is shown with the horizontal-orientation support frame 204, it is understood that any imaging device 102, 202 may be used with any support frame 104, 204 described herein.

In the illustrated embodiments, the spindle mechanism 106, 206 is mounted to an exoskeleton 108, 208 of the imaging device 102, 202. In the illustrated embodiments, each support frame 104, 204 includes a bore 110, 210 that receives the spindle 106, 206 of the imaging device 102, 202 and secures the imaging device 102, 202 to the support frame 104, 204. In other embodiments, alternative mounting mechanisms can be used to secure the imaging device 102, 202 to the respective support frame 104, 204.

Figure 2:
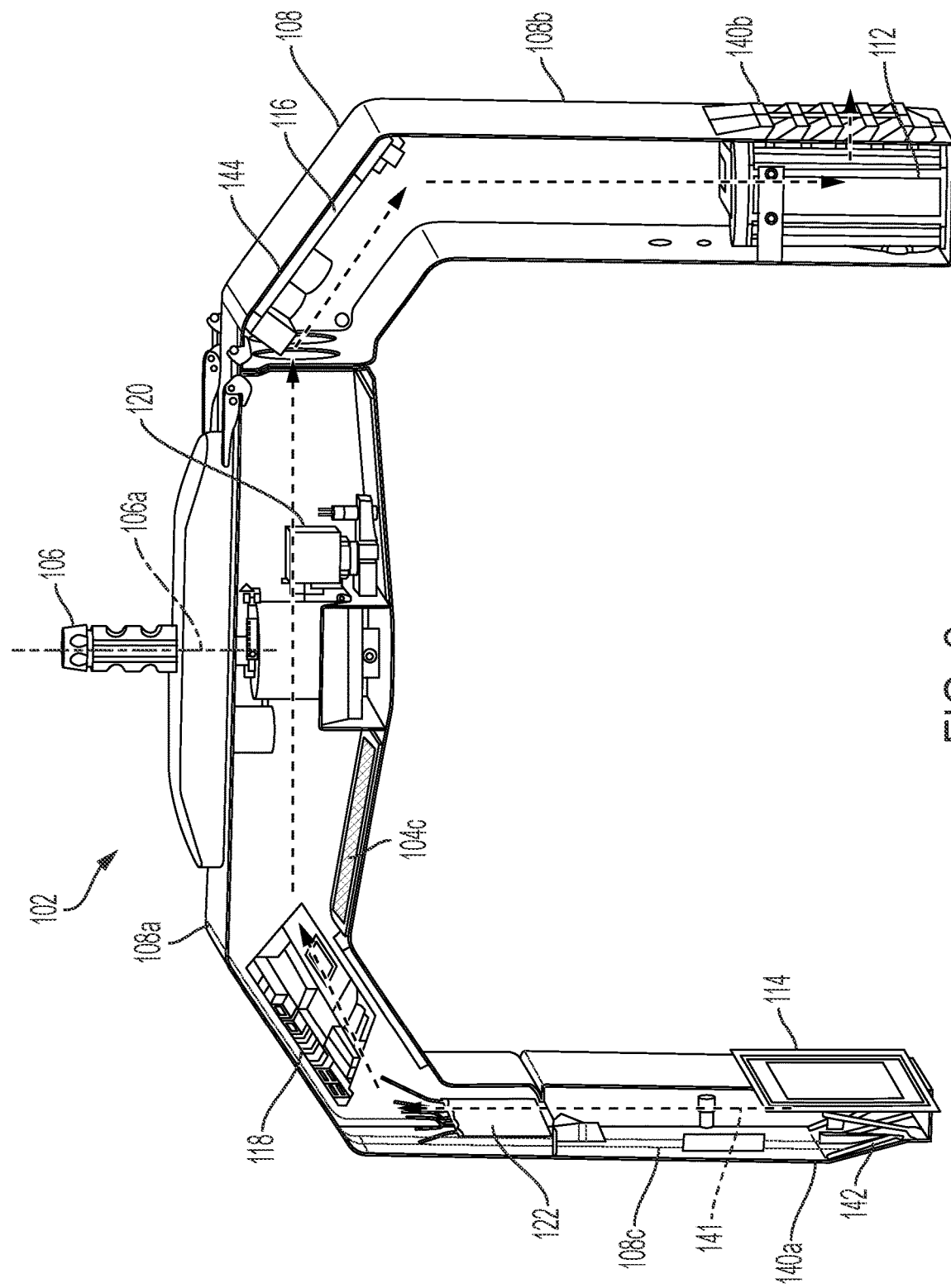
FIG. 2 is a cross-sectional view of the imaging device of FIG. 1.
Figure 3:
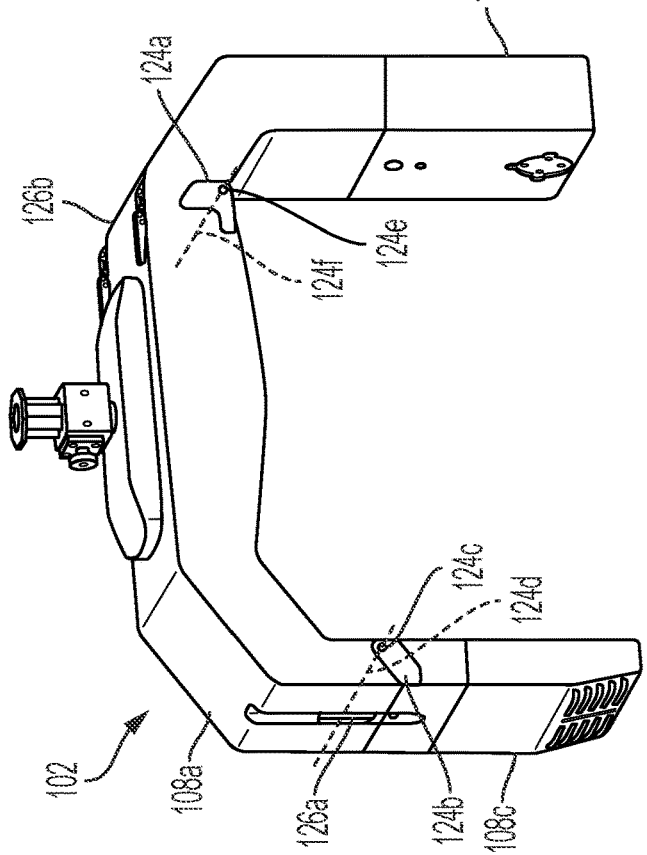
FIG. 3 is a perspective view of the imaging device of FIG. 3, showing an exoskeleton thereof in an unfolded, locked, and operable position.

Referring to FIGS. 1-7, the imaging device 102 is a gantry assembly that includes an exoskeleton 108 comprising a base portion 108a and first and second side portions 108b, 108c. The exoskeleton 108 is movable between an operable position as shown in FIG. 3 and a folded, compact position shown in FIG. 4.

As shown in FIG. 2, components of the imaging device 102 are affixed to internal surfaces of the base portion 108a and side portions 108b, 108c. Affixing the components to the exoskeleton 108 eliminates the need for a metal frame that is required in a conventional imaging system, which ultimately reduces the weight of the imaging device 102. Components may include an x-ray source 112, a detector 114, a circuit board 116, a control PC 118, a rotation motor 120 and an optional Wi-Fi communication module 122, the details of which are disclosed in U.S. Pat. Nos. 7,379,524 and 10,952,688, the entireties of which are incorporate herein by reference. Additional internal components may be incorporated, as will be understood by those skilled in the art based on the present disclosure.

In some embodiments, the components within the imaging device 102 communicate internally wirelessly, such as, for example, through a Bluetooth or Wi-Fi network. The components may also communicate with external devices wirelessly as well and may require an antenna located externally of the exoskeleton 108. In other embodiments, internal communications between components are enabled by wiring that passes through openings in adjacent end surfaces of the base portion 108a, the first side portion 108b, and the second side portion 108c. For example, the openings may be adjacent to the hinge mechanisms 124a, 124b.

In some embodiments, the x-ray source 112 is affixed to an internal outer end of the first side portion 108b and the detector 114 is affixed to an internal outer end of the second side portion 108c so that the x-ray source 112 and the detector 114 are positioned directly across from and facing each other. In some embodiments, the exoskeleton 108 is opaque. The signal transmitted from the x-ray source 112 to the detector 114 can pass through the material of the exoskeleton 108 and provide a clear image. In other embodiments, the exoskeleton 108 includes a window on inwardly-facing surfaces of the outer ends of the first and second side portions 108b, 108c.

FIG. 3 illustrates the operable position of the imaging device 102 in which the base portion 108a and the side portions 108b, 108c are in a locked configuration, forming a gantry assembly.

The base portion 108a includes a generally rectangular section and a corner section. An outer surface of the base portion 108a includes first, second, and third sections. The inner surface includes corresponding first, second, and third sections. Each side of the base portion 108a has a generally polygonal shape that spans the corresponding first, second, and third sections of the outer and inner surfaces.

The first side portion 108b of the exoskeleton 108 has a generally rectangular shape, including an outer surface, an inner surface opposite the outer surface, and side surfaces that span the outer and inner surfaces. An inner first end of the first side portion 108b is adjacent to a first base end of the base portion 108a and opposite to an outer first end of the first side portion 108b.

The second side portion 108c of the exoskeleton 108 has a generally rectangular section and a corner section. An outer surface of the second side portion 108c includes first and second sections. The inner surface includes corresponding first and second sections. Each side of the second side portion 108c has a generally polygonal shape that spans the corresponding first and second sections of the outer and inner surfaces.

It can be appreciated by one of ordinary skill in the art that the exoskeleton 108 may be configured in different ways, such as different geometries and different configurations of the base portion and the first and second side portions.

Figure 4:
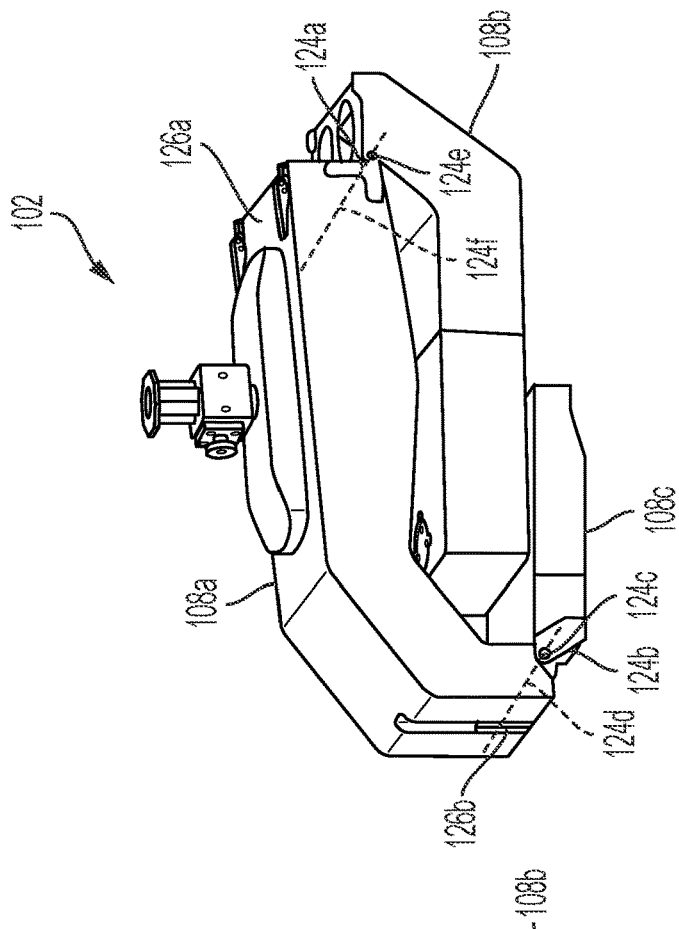
FIG. 4 is a perspective view of the imaging device of FIG. 3, showing the exoskeleton thereof in a folded, locked, and transportable position.

As seen in FIGS. 3 and 4, the base portion 108a and the first and second side portions 108b, 108c may be coupled together using hinge and locking mechanisms 124a, 124b, 126a, 126b so that the first side portion 108b and the second side portion 108c are movable with respect to the base portion 108a.

In the illustrated embodiment, the first side portion 108b of the exoskeleton 108 connects to the first corner section of the base portion 108a through a first hinge mechanism 124a and a locking mechanism 126a. The hinge mechanism 124a includes a pair of bracket and pin assemblies 124c mounted to adjacent surfaces of the first end of the base portion 108a and the inner first end of the first side portion 108b. The pins are positioned along an axis of rotation 124d so that the bracket and pin assemblies enable the first side portion 108b to rotate about the pins and move inwardly under the base portion 108a as shown in FIG. 4.

On the outer surfaces of the first side portion 108b and the base portion 108a, a locking mechanism 126a locks the outer surface of the first side portion 108b to the outer surface of the base portion 108a when locked. When the locking mechanism 126a is unlocked, the first side portion 108b is released and capable of rotating about the axis of rotation 124d defined by the pins.

The second side portion 108c of the exoskeleton connects to the main base section of the base portion 108a through a second hinge mechanism 124b similar to the first hinge mechanism 124a. The pair of bracket and pin assemblies 124e of the second hinge mechanism 124b are mounted to adjacent surfaces of the second end of the base portion 108a and the inner second end of the second side portion 108c. The pins are positioned along an axis of rotation 124f so that the bracket and pin assemblies enable the second side portion 108c to rotate about the pins and move inwardly under the base portion 108a as shown in FIG. 4.

On the outer surfaces of the second side portion 108c and the base portion 108a, a locking mechanism 126b locks the outer surface of the second side portion 108c to the outer surface of the base portion 108a when locked. When the locking mechanism 126b is unlocked, the second side portion 108c is released and capable of rotating about the axis of rotation defined by the pins.

Figure 5A:
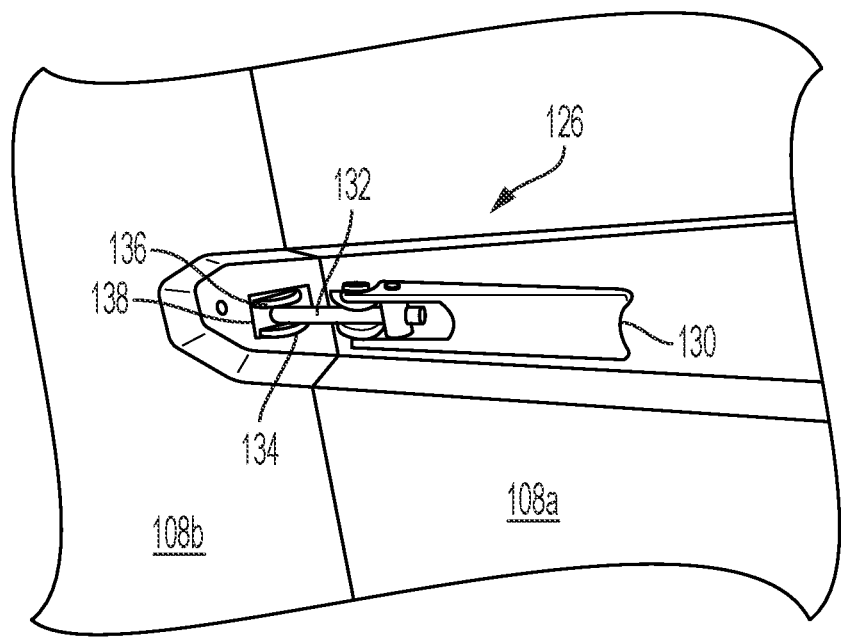
FIGS. 5A and 5B are elevational views of a hinging mechanism of the imaging device of FIG. 3 in a locked and unlocked position.
Figure 5B:
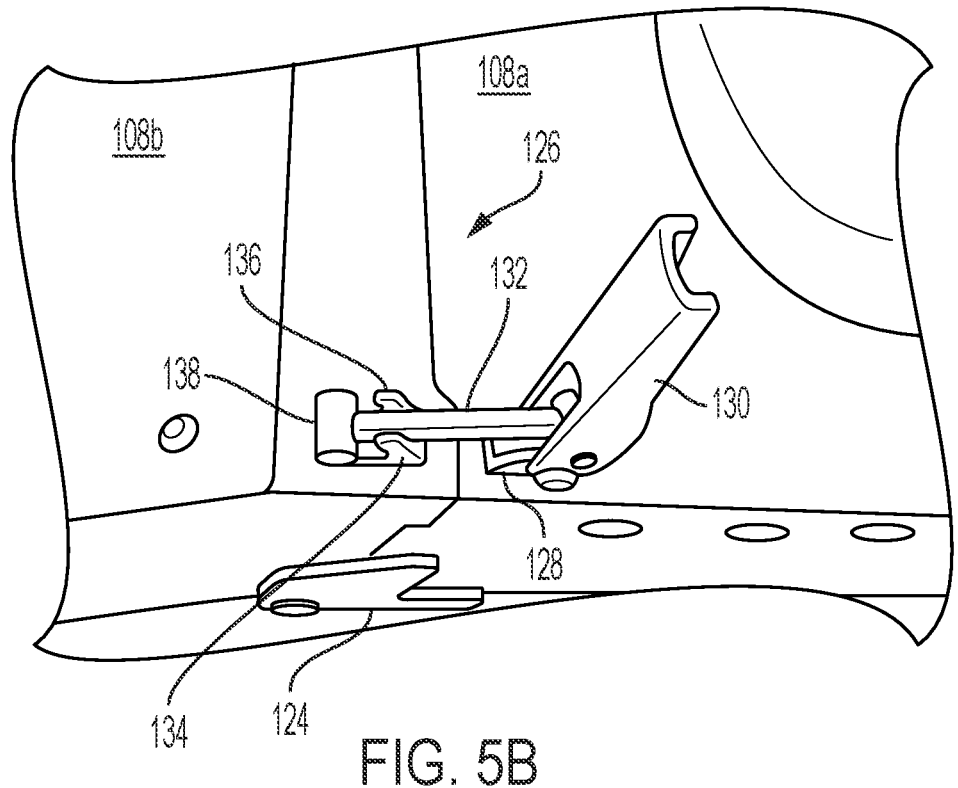

Referring to FIGS. 5A and 5B, the locking mechanism 126 holds the respective side portion 108b, 108c in place relative to the base portion 108a and prevents the side portion 108b, 108c from moving about the hinge assembly 124 when the imaging device 102 is ready for use. The illustrated embodiment includes a rod base 128 (FIG. 5B) secured to the base portion 108a. A lever 130 extends from the rod base 128, and a locking rod 132 extends from a point along the lever 130 distanced from the rod base 128. A receiver base 134 of the locking mechanism 126 is mounted to the first or second side section 108b, 108c (108b in FIGS. 5A and 5B) and includes a hooking portion 136 configured to receive a knob 138 of the locking rod.

During use, the locking rod 132 engages with the receiver base 134 and the lever 130 is pulled down to create enough tension to hold the side portion 108c, 108c in place. When the lever 130 is upright, the knob 136 of the locking rod 132 may be positioned within the hooking portion 136 of the receiver base 134. Movement of the lever 130 toward the outer surface of the base portion 108a causes the knob 138 to pull on the hooking portion 136, creating tension to maintain the knob 138 in the hooking portion 136. When the lever 130 is released and moved into the upright position, tension is released from the locking rod 132 and the knob 138 can move out of the hooking portion 136 of the receiver base, allowing the side portions 108b, 108c to move freely about the hinge.

In other embodiments, any suitable locking mechanism may be used, including, for example, one or more of a locking hinge, a draw or toggle latch, a bolt latch, a cam latch, a spring-loaded clip, or the like.

FIG. 4 illustrates a second position of an imaging device where the base portion 108a and the side portions 108b, 108c are in a folded configuration. Unlocking the locking mechanism 126a, 126b allows the first and second side portions 108b, 108c to fold toward the base portion 108a. In some embodiments, the first side portion 108b is folded first and the second side portion 108c is folded second, with the first side portion 108b being held between the base portion 108a and the second side portion 108c.

The folded configuration of the imaging device 102 packs the imaging device 102 into a compact structure, making it easy to transport. Additionally, the compact nature of the folded configuration requires less space in storage. Specifically, the folded configuration allows for repeatable reconfiguration of the first and second side portions 108b, 108c to a known geometry. As described below, alternative embodiments of the imaging device 102 do not require folding.

Figure 6:
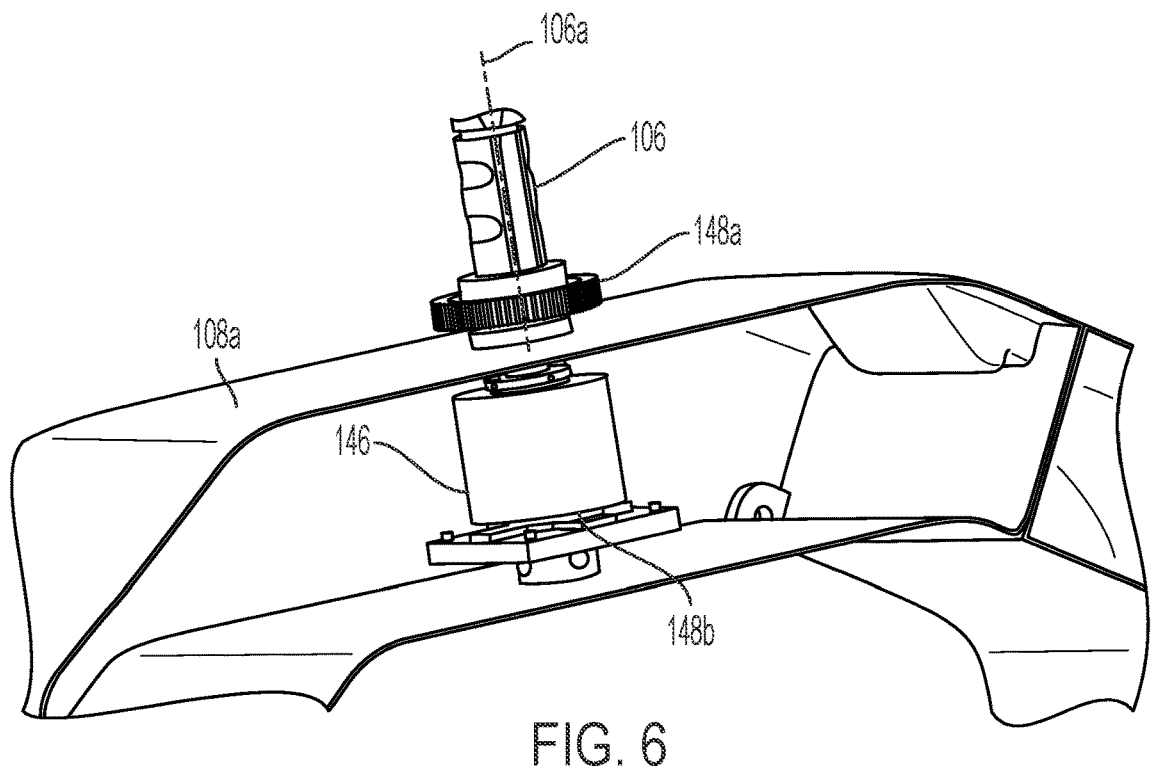
FIG. 6 is a close-up view of the spindle and slip ring of the imaging device of FIG. 3.

Also shown in FIGS. 2 and 6, a centrally-located spindle structure 106 protrudes from the outer surface of the base portion 108a and defines an axis of rotation 106a about which the exoskeleton 108 rotates. FIG. 6 illustrates a close up view of the spindle 106 connected to a slip ring 146 within the exoskeleton 108. The spindle 106 extends through the outer surface of the base portion 108a of the exoskeleton 108. Upper and lower bearings 148a, 148b on each side of the outer surface enable the exoskeleton 108 to rotate about the spindle 106, specifically about the axis of rotation 106a, while the spindle 106 is securely held in place within the support frame 104.

The slip ring 146 conducts electrical signals and power to the imaging components inside the exoskeleton 108. Specifically, the slip ring 146 conducts electrical signals and power between the support frame 104 and the imaging components. During use, the slip ring 146 rotates with the exoskeleton 108 about the axis of rotation 106a relative to the support frame 104, while the spindle structure 106 remains stationary relative to the support frame 104.

In one embodiment, the slip ring 146 comprises a Senring® SNB series Industrial Bus Signal Slip Ring and includes four conductors for USB communication, four conductors for power, and four conductors for control signals/canbus. The slip ring 146 is smaller in size compared to conventional CT scanner slip rings and enables infinite rotation while maintaining conductivity of power and data signals. Use of the slip ring 146 avoids cables twisting and allows the system to spin up to the rates desired for higher speed or multi orbit imaging.

Wiring from the circuit may be affixed and remain stationary as it is fed through a cannula bore in the spindle structure 106 and out holes near the lower bearing. The wiring may then connect to a stationary portion of the slip ring 146 that communicates the electrical signals to a rotating portion the slip ring 146. The imaging device 102 may also include a rotation motor 120 configured to rotate the imaging device 102 about the spindle 106 while the spindle 106 remains stationary. In some embodiments, the rotation motor 120 may be positioned within the base portion 108a of the exoskeleton 108.

In some embodiments, the spindle structure 106 is positioned to ensure proper balancing of the imaging device 102 during use. For example, the spindle structure 106 is positioned so that the weight of the imaging device 102 on one side of the spindle structure 106 is equal to the weight of the imaging device 102 on the other side of the spindle structure 106.

The spindle structure 106 may by cylindrical, cubical, or any suitable geometry to engage with the support frame 104. In some embodiments, the exoskeleton 108 in the operable position may be symmetrical in shape for balancing, while in other embodiments, the exoskeleton 108 is asymmetrical but balanced.

Figure 7:
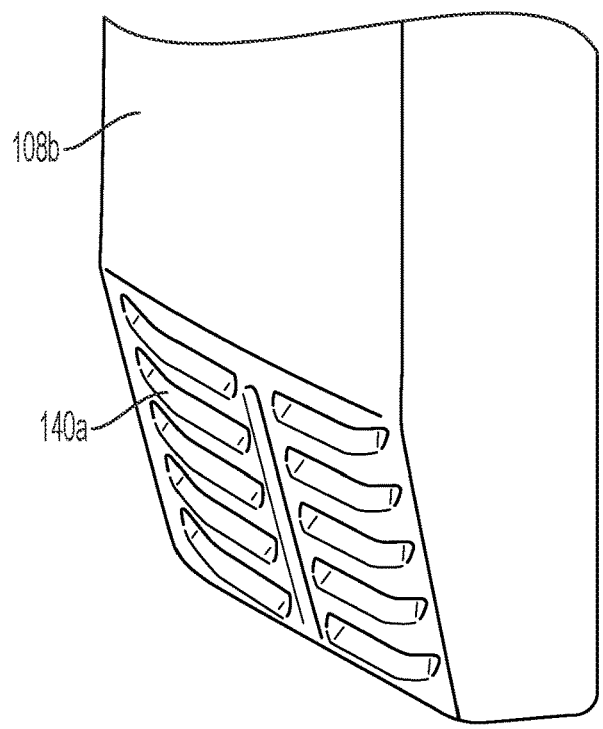
FIG. 7 shows a close-up view of a vent of the imaging device of FIG. 3.

Referring to FIG. 7, the exoskeleton 108 of the imaging device 102 may include one or more vents 140 to ensure proper air flow 141 through the device and prevent overheating of any of the components. For example, an intake vent 140a may be positioned on the outer surface of the second side portion 108c and an outlet vent 140b may be positioned on the outer surface of the first side 108b portion to enable air to flow through the exoskeleton. In some embodiments, an intake fan 142 is provided within the exoskeleton 108 adjacent to the intake vent 140a. In some further embodiment, an additional intake vent 140c may be located on an inner surface of the base portion 108a, such as in the interior of the gantry assembly of the imaging device 102, to increase air flow through the exoskeleton 108. Vents 140 may be positioned in any other suitable location of the exoskeleton 108.

The vents 140 may be configured so that fluid such as rain cannot enter the internal space of the exoskeleton 108. For example, the partitions of the vent 140a, 140b may be angled downward to the outside of the exoskeleton so fluid, such as rain fall, will drain off of the vent 140a, 140b. Additionally, the partitions of the vent 140a, 140b may project from the exterior of the exoskeleton 108 to the interior of the exoskeleton 108 so that the vent does not protrude beyond the exterior surface of the exoskeleton 108 as shown in FIG. 7.

Referring again to FIG. 2, the imaging device 102 may include a grounding plate 144 positioned inside the exoskeleton 108. All of the electrical components of the imaging device 102 may ground to the internal grounding plate 144. The internal grounding plate 144 may also be affixed to the exoskeleton 108, either on the base portion 108a or side portions 108b, 108c, using non-conductive material. The grounding plate 144 may be constructed of a metallic material, such as copper, aluminum, or steel.

The exoskeleton 108 may be made of a light weight and sturdy material so the medical imagining device 102 is easily transported and the inside components are protected. In some embodiments, the imaging device 102 weighs less than 70 pounds. Additionally, the exoskeleton 108 may be made of a material that allows unattenuated transmission of both x-rays and wireless signals, which are needed to control the imaging device 102 remotely. For example, the exoskeleton 108 may be constructed of a plastic, carbon fiber, fiber glass, or any other suitable material.

An alternative embodiment of the imaging device 202 is illustrated in FIGS. 11-13. The imaging device 202 is similar to the imaging device 102 with the exception that the first and second side portions 108b, 108c of the exoskeleton are formed integrally with the base portion 108a and do not rotate into a folded position. The imaging device 202 does not include hinge and locking mechanisms 124, 126 to enable rotation of the first and second side portions 108b, 108c, and therefore does not move between a folded, transportable position and an unfolded, operable position. Similar to the imaging device 102, the imaging device 202 includes an exoskeleton 208 onto which the imaging components are affixed, eliminating the need for an internal frame and the associated unnecessary weight.

Further, the exoskeleton 108, 208 may have a shape other than a gantry with arms. For example, the exoskeleton 108, 208 may include a ring-shaped portion onto which imaging components such as the x-ray source and the detector are affixed. Similar to the previously described embodiments, the ring-shaped portion rotates about the spindle structure. In other embodiments, the exoskeleton 108, 208 may have a cuboidal shape with a blind cavity or bore extending fully therethrough. Other shapes and sizes may be used as desired.

Figure 9:
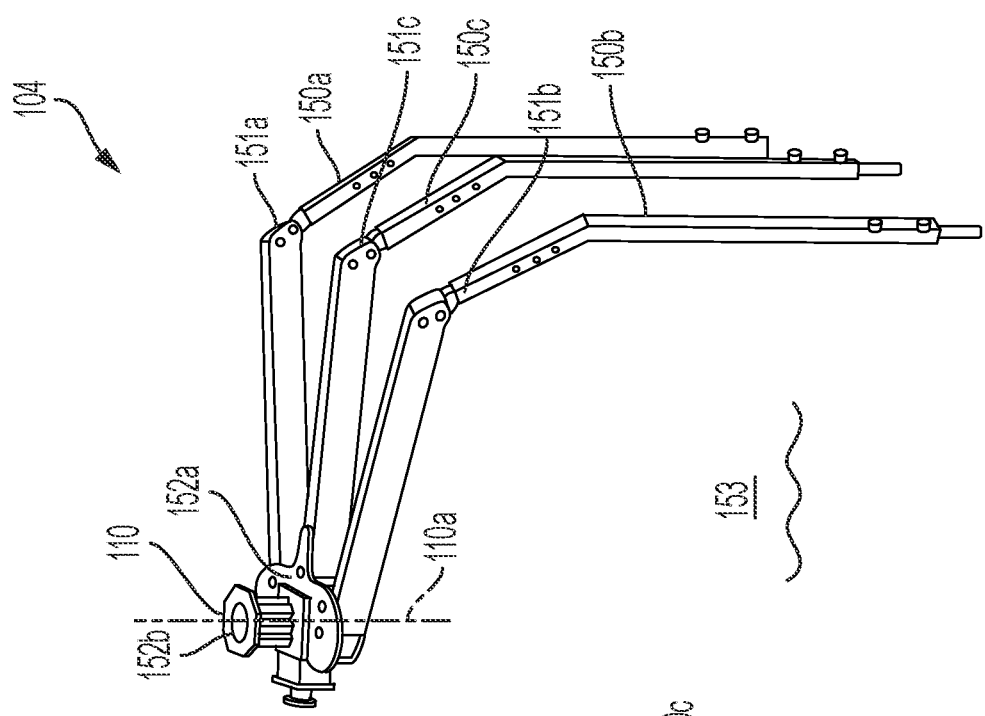
FIG. 9 shows the support frame of FIG. 1 transitioning from the operable position to a stored position.
Figure 8:
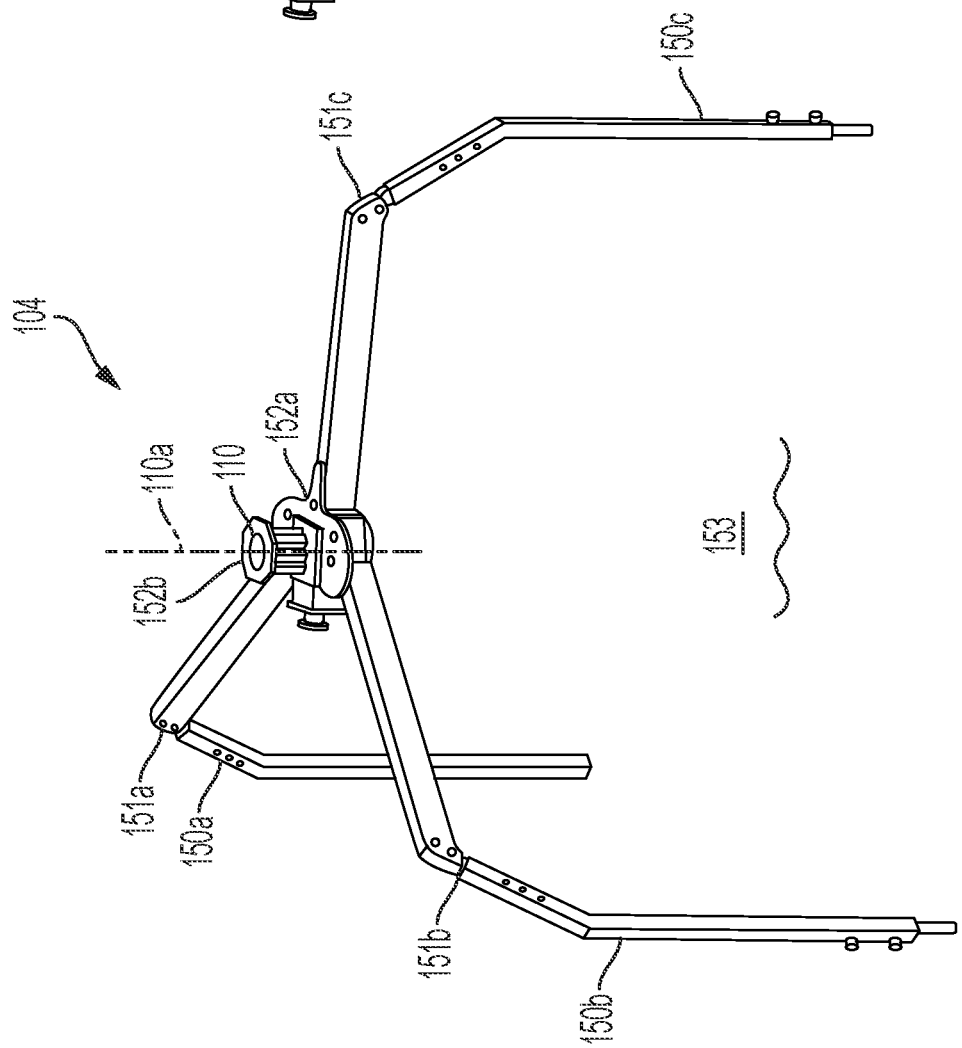
FIG. 8 shows the support frame of FIG. 1 in an operable position.
Figure 10:
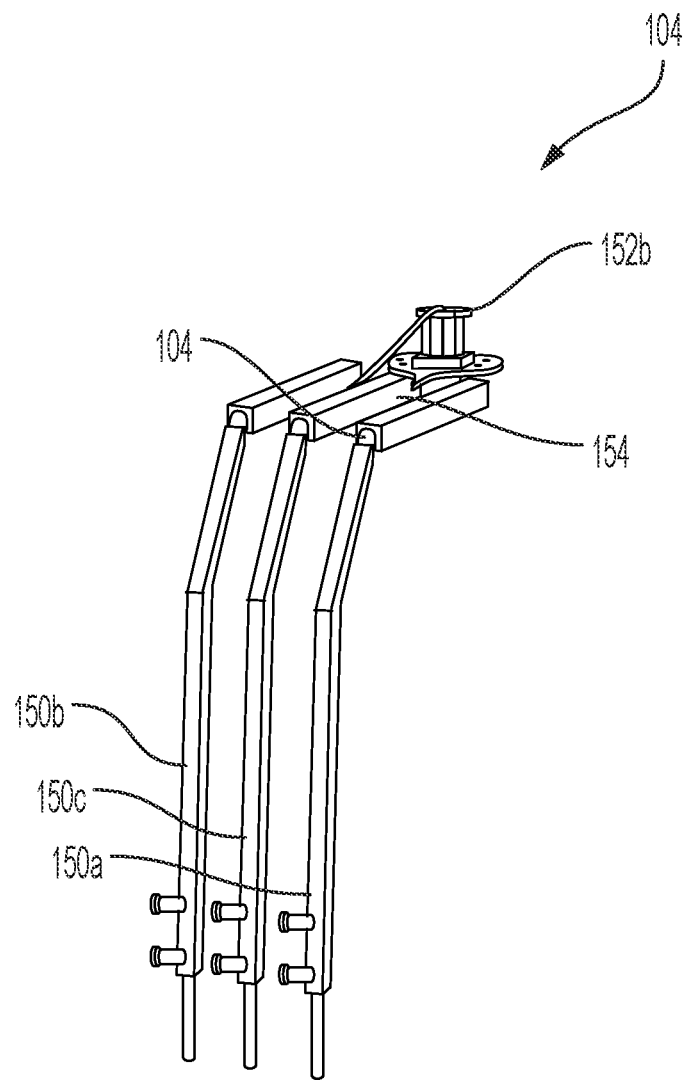
FIG. 10 shows the support frame of FIG. 1 in the stored position.

FIGS. 8-10 illustrate the example support frame 104, while FIGS. 11-13 illustrate the alternative support frame 204. During use, the support frame 104, 204 rests on a support surface, such as the ground, the floor of an ambulance, the floor of a plane, etc. In some embodiments, such as the embodiment of FIGS. 8-10, a bore 110 of the support frame has a central axis that extends perpendicular to the support surface on which the support frame 104 rests. In other embodiments, such as the embodiment of FIGS. 11-13, the bore 210 of the support frame 202 has a central axis that extends parallel to the support surface on which the support frame 202 rests. In still further embodiments, the bore 110, 210 of the support frame 102, 202 can have a central axis that extends in any angle relative to the support surface on which the support frame rests.

The portable imaging device 102, 202 and the support structure 104, 204 may be detachable with respect to each other to allow for easy transportation of both the imaging device 102, 202 and the support structure 104, 204 separately. In some embodiments, the support frame 104, 204 and the medical imagining device 102 may be transported while still attached and/or in a connected configuration.

As shown in FIGS. FIGS. 8-10, the support frame 104 includes a plurality of legs 150a, 150b, 150c extending from a bracket 152. The bore 110 of the support frame 104 has a central axis 110a that extends perpendicular to the support surface 153 on which it rests. This results in the open side of the gantry assembly of the imaging device 102 to face down toward the support surface 153. The plurality of legs 150a, 150b, 150c can extend around the imaging device 102 leaving enough room between the legs 150a, 150b, 150c and the exoskeleton 108 of the device 102 to allow the imaging device 102 to rotate completely within the plurality of legs 150a, 150b, 150c. The imaging device 102 is also able to hang from the bore 110 so that the imaging device 102 is free standing.

The bracket 152 of the support frame may include a base 152a and a bushing 152b, with the bore 110 of the support frame 104 extending through the length of the base 152a and the bushing 152b. The plurality of legs 150a, 150b, 150c may rotate about the bracket 152 from an operable to a stored position and vice versa. FIGS. 8-10 show the support system 104 in an operable position, transitioning into a storage position, and the storage position, respectively.

Each leg of the plurality of legs 150 includes an inner end positioned within the bracket 152 and an outer end opposite the inner end. The plurality of legs 150 can include multiple segments connected by hinges 151a, 151b, 151c that are foldable with respect to each other. The folding nature of the legs 150 allows a user to adjust the positioning of the support frame 104, providing greater user control when adjusting the imaging device 102 onto an uneven surface, for example. Upon the weight of the imaging device 102 engaging with the support frame 104, the hinges 151a, 151b, 151c lock into position, becoming rigid to support the weight of the imaging device 102.

FIG. 10 illustrates the support frame 104 in the stored configuration. The legs 150a, 150b, 150c of the support frame 104 are moved to extend over one side of the external part of the exoskeleton 108. Additionally, a handle 154 may extend from the bushing to be grasped by a user during transportation.

FIGS. 11-13 show another example support frame 204. As discussed previously, the support frame 204 may be a cart with a base portion 204a and a side portion 204b perpendicular thereto. A bore 210 configured to engage with the imaging device 102 may be positioned on the side portion 204b of the support frame 204. A central axis 210a defined by the bore 210 is parallel to the support surface 253 on which the support frame 204 rests. This configuration results in the open side of the gantry assembly to face to the side in relation to the support surface 253. The cart 204 may include one or more wheels 256a, 256b, 256c, 256d for transportation. In some embodiments, the cart does not include wheels 256 or includes removable wheels. The cart 204 may also be foldable, for instance, the side portion 204b may fold into the base portion 204a to create a compact structure for storage.

As illustrated, the side portion 204b of the support frame may be perpendicular to the base portion 204a of the support frame 204. The side portion 204b extends upwardly from the base portion 204a at mounting position 204a-1 along a width of the base portion 204a between first and second ends 204a-2, 204a-3 thereof. First and second sets of braces 212a, 212b extend from the side portion 204b toward the first and second ends 204a-2, 204a-3, respectively, of the base portion 204a. The mounting position 204a-1 and the positioning and sizing of the first and second sets of braces 212a, 212b are selected to provide sufficient support for the imaging device 102, 202 mounted onto the support frame 202.

The base portion 204a of the support frame 204 and the side portion 204b of the support frame 204 may be any suitable shape to provide support for the support frame 204. The bore 210 configured to receive the imaging device 202 is positioned on an upper edge of the side portion 204b of the support frame 204. In other embodiments, the imaging device 202 is mounted to the support frame 204 through other suitable attachment means.

Figure 14:
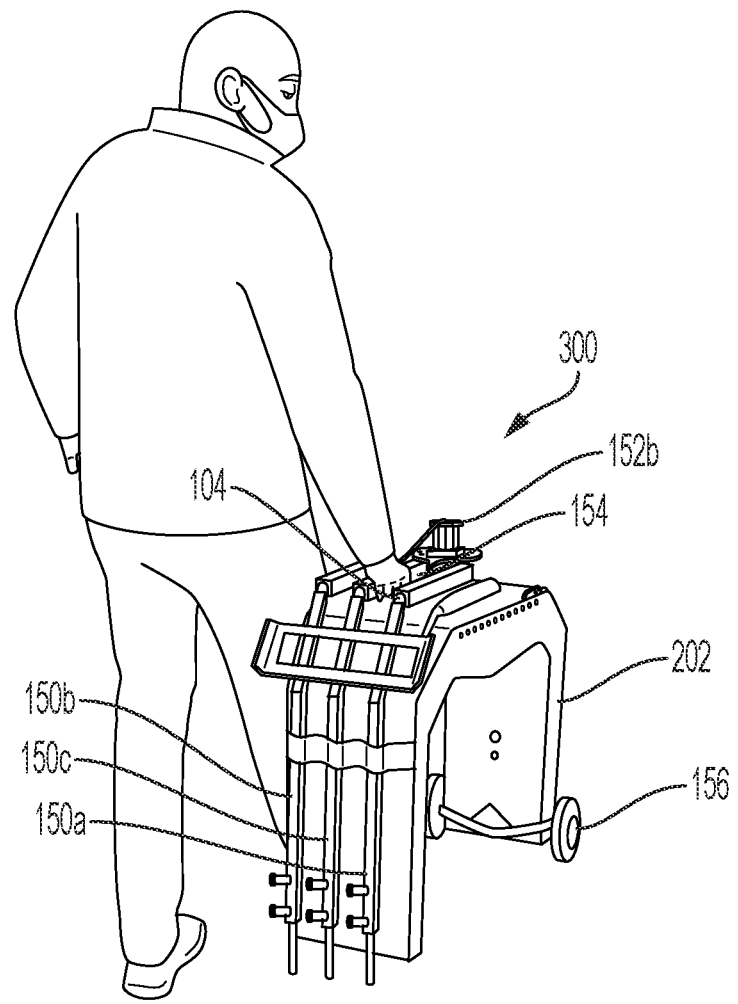
FIG. 14 shows the support frame of FIGS. 9-11 in the stored position transporting the imaging device of FIG. 11.

FIG. 14 illustrates an example imaging system 300 including the imaging device 202 secured within the support frame 104 in the storage position and being transported together. In this embodiment, each leg 150a, 150b, 150c of the support frame 104 is secured to the exoskeleton 208 by any suitable securing mechanism, for instance by tying or clipping the legs 150 to the exoskeleton 108. The plurality of legs 150*a*, 150*b*, 150*c* may have the same outside shape as half of the exoskeleton 208 so that the imaging system 300 is easy to transport without any protruding elements.

In the embodiment illustrated in FIG. 14, a side portion of the imaging device 202 rests on a wheeled surface 156 for easy transportation. In other embodiments, the imaging device 202 may include wheels on one or both side portions to allow the medical imagining device 202 to be easily transported. In some embodiments, the wheel 156 is removable from the imagining device 202 during use and is attachable to the imaging device 202 for transportation.

Figure 15:
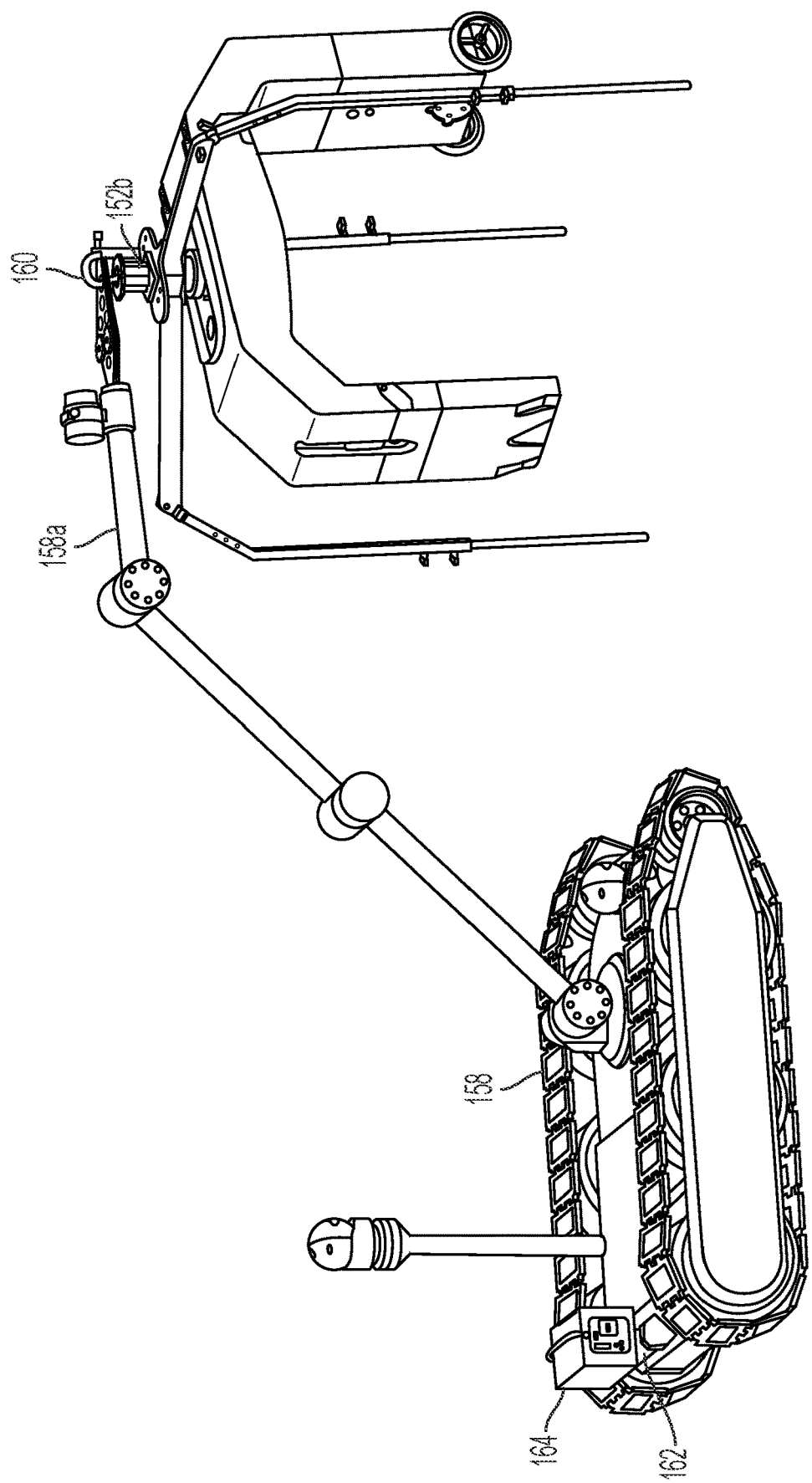
FIG. 15 shows a perspective view of the imaging system of FIG. 1 held by a robot.

Referring to FIG. 15, a robot 158 or other suitable machine may be used to transport, relocate, or otherwise move an imaging system 100, 200, 300 according to the present disclosure. The imaging system 100, 200, 300 may include a hook 160 for receiving an arm 158*a* of the robot 158. For example, the hook 160 may extend from or couple to the bushing 152*b* of the support frame 104. Alternatively, the robot arm 158*a* can hold a hook 160 on the exoskeleton 108 of the imaging device 102 directly and act as a support structure during operation of the device.

In some embodiments, the robot 158 is a remote-controlled robot, such as a military robot or ANDROS F6A. A tray 162, such as a mini trailer hitch, may be mounted to the back of the robot and may be configured to hold and secure a power supply 164 of the imaging device 102. The mounted power supply 164 acts as a counterweight to balance out the weight of the imaging device 102 and also removes weight from the imaging device 102.

Another aspect of the disclosure provides a method of acquiring an image using the imaging device 102, 202 as disclosed herein. The method includes positioning the imaging system 100, 200, 300 and capturing an image using the imaging device 102, 202. The imaging system 100, 200, 300 can be positioned around a target object or a patient or injured person either physically by a user, by a robot, by a user remotely, or combinations thereof.

Capturing an image may include capturing a single x-ray projection image. In another embodiment, capturing an image means capturing a single x-ray projection image, adjusting the imaging device 102, 202 to a different angle, capturing another x-ray projection image, and repeating until all of the necessary images are obtained. Capturing an image can also refer to a full CT scan, in which the imaging device 102, 202 rotates 360 degrees about the object and collects a plurality of x-ray projection images that are used to generate a volumetric CT scan, or fluoroscopic imaging. Another method of capturing an image includes a partial CT scan, in which a CT scan is performed with less than 360 degree rotation.

The method may additionally include transmitting the images to a remote user either wirelessly or through a wired connection. After transmission, the imaging system 100, 200, 300 may be folded and stored for later use.

We claim:

1. An imaging device comprising:
   an exoskeleton configured to house and provide structural support for an x-ray source and a detector;
   a spindle structure protruding from an outer surface of the exoskeleton;
   the x-ray source affixed to an internal surface of the exoskeleton;
   the detector affixed to the internal surface of the exoskeleton;
   a rotation motor configured to rotate the exoskeleton about the spindle structure; and
   a circuit board, a control PC, and a Wi-Fi communication module, wherein the circuit board, the control PC, and the Wi-Fi communication module are provided within the exoskeleton, and wherein the Wi-Fi communication module includes an antenna external to the exoskeleton.

2. The imaging device of claim 1, wherein the exoskeleton includes a base portion, a first side portion, and a second side portion.

3. The imaging device of claim 2, wherein at least one of the first side portion or the second side portion connects to the base portion through a hinge mechanism.

4. The imaging device of claim 3, further comprising a locking mechanism configured to prevent the at least one of the first side portion or the second side portion from moving about the hinge mechanism.

5. The imaging device of claim 2, wherein the first side portion and the second side portion are configured to fold towards the base portion.

6. The imaging device of claim 2, wherein the spindle structure extends through the outer surface of the base portion.

7. The imaging device of claim 1, further comprising a slip ring connected to the spindle structure and configured to conduct electrical signals and power to imaging components within the exoskeleton.

8. The imaging device of claim 1, further comprising a support frame including a bracket and a plurality of legs, each leg rotatably connected to the bracket, wherein the support frame is configured to move between an operable position and a stored position.

9. The imaging device of claim 1, wherein the exoskeleton comprises one of plastic, carbon fiber, and fiber glass.

10. An imaging system comprising:
    an imaging device including:
       an exoskeleton configured to house and provide structural support for an x-ray source and a detector;
       a spindle structure protruding from an outer surface of the exoskeleton and defining an axis of rotation, wherein the exoskeleton rotates about an axis of rotation;
       an x-ray source affixed to an internal surface of the exoskeleton;
       a detector affixed to the internal surface of the exoskeleton; and
       a rotation motor configured to rotate the exoskeleton about the spindle structure; and
    a support frame configured to receive the spindle structure of the exoskeleton,
    wherein the support frame is positioned on a support surface, wherein the axis of rotation extends perpendicular to the support surface,
    wherein the support frame includes a plurality of legs extending from a bracket, wherein the plurality of legs moves between an operable position and a stored position, and wherein a bore extends through the bracket, and
    wherein the bracket includes a bushing attached to a base, wherein the bore extends through the base and bushing, wherein each leg includes an inner end and an outer end, and wherein the inner ends of the plurality of legs are secured in the base and circumscribe the bushing when the plurality of legs is in the operable position.

11. The imaging system of claim 10, wherein the exoskeleton includes a base portion, a first side portion, and a second side portion.

12. The imaging system of claim 10, wherein the support frame is positioned on a support surface, and wherein the axis of rotation extends parallel to the support surface.

13. A method of acquiring a scan of a target object, the method comprising:
providing an imaging system comprising:
an imaging device comprising:
an exoskeleton configured to house and provide structural support for an x-ray source and a detector;
a spindle structure on an outer surface of the exoskeleton and defining an axis of rotation;
an x-ray source affixed to an internal surface of the exoskeleton;
a detector mounted affixed to the internal surface of the exoskeleton; and
a rotation motor configured to rotate the exoskeleton about the spindle structure; and
a circuit board, a control PC, and a Wi-Fi communication module, wherein the circuit board, the control PC, and the Wi-Fi communication module are provided within the exoskeleton, and wherein the Wi-Fi communication module includes an antenna external to the exoskeleton; and
a support frame configured to receive the spindle structure of the exoskeleton;
securing the imaging device within the support frame;
positioning the target object within the imaging device;
capturing an image of the target object using the x-ray source and the detector of the imaging device.

14. The method of claim 13, wherein capturing an image comprises capturing at least one x-ray projection image that includes static or dynamic features of the target object.

15. The method of claim 13, further comprising rotating the exoskeleton about the axis of rotation, wherein capturing an image comprises capturing a plurality of x-ray projection images as the exoskeleton rotates about the axis of rotation.

16. The method of claim 15, further comprising tomographically reconstructing the plurality of x-ray projection images into a CT image volume.

* * * * *